United States Patent [19]

Kowalski

[11] Patent Number: 5,821,049
[45] Date of Patent: Oct. 13, 1998

[54] IN VITRO ASSAY FOR IDENTIFICATION OF CARCINOGENS

[75] Inventor: Linda A. Kowalski, Vancouver, Canada

[73] Assignee: Viratest Carcinogen Monitoring, Ltd, Vancouver, Canada

[21] Appl. No.: 628,758

[22] Filed: Apr. 5, 1996

[51] Int. Cl.[6] .............................. C12Q 1/70; C12Q 1/68; G01N 33/574; C12N 1/20
[52] U.S. Cl. ................... 435/5; 435/6; 435/7.23; 435/29; 435/252.3; 436/63; 436/64
[58] Field of Search ................... 435/7.23, 5, 6, 435/29, 252.3; 436/63, 64

[56] References Cited

U.S. PATENT DOCUMENTS

| | | | |
|---|---|---|---|
| 5,273,880 | 12/1993 | Schiestl | 435/6 |
| 5,330,896 | 7/1994 | Billing | 435/7.23 |
| 5,336,613 | 8/1994 | Niwa et al. | 435/228 |
| 5,347,075 | 9/1994 | Sorge | 800/2 |
| 5,356,806 | 10/1994 | Harris et al. | 435/240.2 |
| 5,376,542 | 12/1994 | Schlegal | 435/172.2 |
| 5,382,510 | 1/1995 | Levine et al. | 435/6 |
| 5,387,508 | 2/1995 | Jaffe | 435/32 |
| 5,413,915 | 5/1995 | Case et al. | 435/25 |

FOREIGN PATENT DOCUMENTS 1292928  10/1991  Canada .

OTHER PUBLICATIONS

Casto et al, "Enhancement of viral transformation for evaluation of the carcinogenic or mutagenic potential of inorganic metal salts" Cancer Research, vol. 39, pp. 193–198, Jan. 1979.

Isfort et al, "Application of in vitro cell transformation assays to predict the carcinogenic potential of chemicals" Mutation Research, vol. 365, pp. 161–173, 1996.

Amtmann et al., 182, Nature, 296:675–677.

Kowalski et al., 1992, Cancer Lett., 64:83–90.

Stich et al., 1989, Cancer Lett., 45:71–77.

Tsang et al., 1988, Cancer Lett., 43:93–98.

Tsang et al., 1991, Cancer Det. Prev., 15(5):423–427.

Traul et al., 1979, Int. J. Cancer, 23:193–196.

Primary Examiner—Sheela Huff
Assistant Examiner—Yvonne Eyler
Attorney, Agent, or Firm—Sheridan Ross P.C.

[57] ABSTRACT

Disclosed is a method to evaluate the carcinogenicity of a compound using a transformation assay. The method includes contacting a compound to be tested for carcinogenicity with a test cell. The test cell either includes a recombinant isolated nucleic acid molecule which encodes a cellular transforming protein or a modified genome which encodes a cellular transforming protein. Cell growth is scored to identify the presence or absence of a transformation characteristic, such as formation of foci, loss of growth factor or serum requirements or anchorage independence. The development of such a transformation characteristic indicates that the compound being tested is carcinogenic. Cellular transforming proteins of the present invention can include growth factors, growth factor receptors, intracellular transducers and nuclear transcription factors. Further embodiments include a method to evaluate the anticarcinogenicity of a compound, which includes contacting a compound to be tested for anticarcinogenicity with a test cell under conditions which, in the absence of the compound, the test cell is transformed.

22 Claims, No Drawings

IN VITRO ASSAY FOR IDENTIFICATION OF CARCINOGENS

FIELD OF THE INVENTION

The present invention relates to assays for the identification of carcinogenic compounds, and particularly transformation assays, recombinant cells and molecules, and cells with modified genomes useful therefor.

BACKGROUND OF THE INVENTION

New chemicals are constantly produced either for consumer use or as by-products into the environment. These potential human carcinogens are tested in cultures of prokaryotes or lower eukaryotes, in living rodents and in mammalian cells in tissue culture. Although these tests are reproducible, reliable, quick, relatively inexpensive and do not sacrifice higher animals, they are inadequate for testing human carcinogens.

Current assays rely on mutagenicity or genotoxicity to identify carcinogens because historically, only mutagens were believed to be carcinogens. Nevertheless, not all carcinogens are mutagens. Mutagenic carcinogens are usually electrophiles or capable of metabolic conversion to electrophiles which attack DNA causing base alteration and mutation. Nonmutagenic carcinogens induce cell proliferation and DNA synthesis by a variety of biochemical mechanisms eventually resulting in genome alteration; but they are not initially mutagenic. Some metal cations such as vanadate act as mitogens or alter protein phosphorylation. The International Agency for Research on Cancer (IARC) has identified twenty-three chemicals and groups of chemicals which are causally associated with cancer in humans. Of these, arsenic compounds, diethylstilbestrol and others are only weakly mutagenic.

Cell transformation assays can detect both mutagenic and nonmutagenic carcinogens. Therefore, presumably, a chemical that induces or promotes transformation is a carcinogen or tumor promoter. To investigate chemical carcinogenesis and mechanisms or transformation, several assays have been developed which rely on cell transformation. (See, e.g., DiPaolo, J. A. et al. (1969) "Quantitative Studies of in vitro Transformation by Chemical Carcinogens," *J. Natl. Cancer Inst.*, 42:867; Reznikoff, C. A. et al. (1973) "Establishment and Characterization of a Cloned Line of C3H Mouse Embryo Cells Sensitive to Postconfluence Inhibition of Cell Division," *Cancer Res.* 33:3231; Kakunaga, T. (1973) "A Quantitative System for Assay of Malignant Transformation by Chemical Carcinogens Using a Clone Derived from BALB/c3T3," *Intl. J. Cancer,* 12:463). Transformed foci are the endpoint in these assays.

These tests, however, suffer from lack of reproducibility from laboratory to laboratory, technical difficulties, and difficulties in scoring foci as there are several different types of foci. Due to the low transformation frequency, large numbers of plates must be used to obtain statistically significant results for weak carcinogens. The C3H/10T½ assay requires six or more weeks of incubation before foci can be scored, increasing the loss of data due to contamination. Assays using cell transformation, nevertheless, respond to nongenotoxic carcinogens such as hormones and metals.

All virally-enhanced transformation assays have similar problems which compromise their usefulness. These include: variation in transformation frequency among various lots of cells, differing sensitivity to transfection and to carcinogens, variable rates of spontaneous transformation, technical complexity and limited commercial availability.

Therefore, there exists a need for improved transformation assays for rapid and reliable screening for carcinogens.

SUMMARY OF THE INVENTION

The present invention includes a transformation assay to evaluate the carcinogenicity of a compound. The assay includes contacting a test cell with a compound being tested for carcinogenicity. The test cell is a test cell comprising either a recombinant isolated nucleic acid molecule encoding a cellular transforming protein or a modified genome encoding a cellular transforming protein. The method further includes scoring cell growth of the test cell based on identification of transformation characteristics. A positive transformation characteristic indicates that the compound is carcinogenic. Transformation characteristics can include the formation of foci, loss of growth factor or serum requirements, or anchorage independence.

The cellular transforming proteins can be selected from the group of proteins having a function in or which initiate the mitotic cascade which causes transformation of cells from normal cells to cells having aberrant growth properties. In a further embodiment, the cellular transforming protein can be selected from growth factors, growth factor receptors, intracellular transducers, and nuclear transcription factors. The isolated nucleic acid molecule is preferably derived from a virus and in particular, a papilloma virus, such as a bovine papilloma virus (BPV). In particular, the isolated nucleic acid molecule can be derived from a BPV E5, E6 or E7 open reading frame.

In a further embodiment, the present invention includes a method to identify anticarcinogenic compounds. In one embodiment, this method includes contacting a test cell with a compound being tested for anticarcinogenicity. The test cell comprises either a recombinant isolated nucleic acid molecule which encodes a cellular transforming protein or a modified genome which encodes a cellular transforming protein. In one embodiment, the test cell is contacted with the putative anticarcinogenic compound in the presence of a known carcinogen. The method further includes scoring cell growth of the test cell based on identification of a transformation characteristic. The absence of a transformation characteristic indicates that the compound being tested is anticarcinogenic.

In another embodiment of a method to identify anticarcinogenic compounds, the test cell, which has the phenotype of being transformed in the absence of carcinogens, is contacted with the putative anticarcinogenic compound. The absence or reduction of a transformation characteristic indicates that the compound being tested is anticarcinogenic.

DETAILED DESCRIPTION

The present invention involves an in vitro assay for identifying compounds which are carcinogenic, as well as cells and recombinant molecules useful for such assays. The assay method of the present invention is a transformation assay. As such, the method involves contacting a cell of the present invention with a compound being tested for carcinogenicity and identifying whether the compound causes transformation of a cell having normal growth to a cell having abnormal or altered growth properties. Various aspects of transformed cells and identifying characteristics of transformation are discussed in more detail below.

A significant advantage of the present invention, because it involves a transformation assay, is that it is capable of identifying nongenotoxic carcinogens as well as genotoxic carcinogens. For example, the well-known Ames test only detects genotoxic carcinogens (i.e., mutagens). One option for identifying non-genotoxic carcinogens is by animal testing. However, animal testing is relatively expensive and time-consuming. Mutagenic carcinogens are usually electrophiles or are capable of metabolic conversion to electrophiles which attack DNA, causing base alteration and mutation. Non-genotoxic carcinogens induce cell proliferation and DNA synthesis by a variety of biochemical mechanisms eventually resulting in genome alteration; but they are not initially mutagenic. Non-genotoxic carcinogens can include metal cations such as vanadate, which act as mitogens or which alter protein phosphorylation.

The present invention provides many significant advantages over other known assays for identifying carcinogenic compounds and in particular, over other known transformation assays. Specifically, the present invention provides a test cell having an enhanced transformation response in the presence of carcinogens compared to normal or wild-type cells; provides cell lines with stable copy numbers of introduced nucleic acid molecules; provides cell lines which are genetically stable over repeated passaging; provides cell lines with uniform transformation frequency; has short incubation times; and has easily scored endpoints.

An important characteristic of the present invention is that the cells which form the basis for the assay have either (1) a recombinant isolated nucleic acid molecule that encodes a protein involved in the transformation of a cell or (2) a modified genome that encodes a protein involved in the transformation of a cell. Such nucleic acid molecules and modified genomes are more particularly described below. That is, such proteins are involved in the transformation of normal cells to transformed cells. As used herein, a cell is considered to be transformed when, after it has been subjected to a carcinogenic agent in cell culture, it has developed aberrant growth properties or characteristics. Such transformation characteristics can include any properties associated with tumor or cancer cells. In particular, such characteristics can include formation of foci, loss of growth factor or serum requirements and/or anchorage independence. The presence of one or more of such transformation characteristics is indicative that the compound being tested is carcinogenic.

One transformation characteristic is when a cell, which normally does not form a focus, forms a focus when grown on a culture dish. Such cells, when not transformed, typically grow in a flat and organized pattern until they cover the surface of a Petri plate with liquid medium on top of them. Then, when each cell is touching its neighbor cell, cell growth stops by virtue of a phenomenon known as contact inhibition. Such cells, when transformed, are not contact inhibited and will grow to high densities in disorganized foci.

A further transformation characteristic which is indicative of a cell being transformed by a carcinogenic compound is cells becoming anchorage independent. When anchorage independence is the transformation characteristic being used in a particular assay, the cells used in the assay are cells which, when not transformed, are anchorage dependent. That is, when such cells are not transformed, they grow only when attached to a solid surface. Upon becoming transformed, such cells will grow in a medium without being attached to a solid surface.

A further transformation characteristic which is useful in assays of the present invention is the loss of growth factor or serum requirements. Cells used in assays of the present invention in which loss of growth factor or serum requirements is the transformation characteristic, when not transformed, require the presence of isolated growth factors or serum for growth. Upon transformation, such cells are able to grow in the absence of the growth factors or serum required by the untransformed cells.

The assay of the present invention includes contacting a test cell, such as a recombinant cell or a cell with a modified genome, with a compound being tested for carcinogenicity. For example, test cells can be grown in liquid culture medium or grown on solid medium in which the liquid medium or the solid medium contains the compound to be tested. In addition, the liquid or solid medium contains components necessary for cell growth, such as assimilable carbon, nitrogen and micro-nutrients. As used herein, a test cell can be a cell that has either (1) a modified genome that encodes a protein involved in the transformation of a cell or (2) a recombinant isolated nucleic acid molecule that encodes a protein involved in the transformation of a cell. A cell, referred to herein as a recombinant cell, that has the above-mentioned recombinant isolated nucleic acid molecule includes a transfected cell, as well as the progeny of transfected cells, such as a cell that has stably integrated said nucleic acid molecule over generations of repeated cloning and selection.

The assay involves contacting cells with the compound being tested for a sufficient time to allow for transformation of cells in the presence of carcinogenic compounds. The period of contact with the compound being tested can be either the entire growth phase of the assay prior to scoring or some smaller portion thereof. For example, it may be that for more toxic substances a shorter time of contact with the substance being tested is suitable. As used herein, the term "contact period" refers to the time period during which cells are in contact with the compound being tested. The term "incubation period" refers to the entire time during which cells are allowed to grow prior to scoring. Thus, the incubation period includes all of the contact period and may include a further time period during which the compound being tested is not present but during which growth is continuing prior to scoring.

After the incubation period, cell growth is scored for the presence or absence of one or more transformation indicators. The appearance of transformed cells in the present invention, as indicated by the presence of one or more transformation indicators, is considered to be indicative that the compound tested by the assay of the present invention is likely to be carcinogenic.

In the instance of the transformation characteristic being the formation of foci, cells can be stained and examined visually or with the aid of a microscope. The presence of foci on culture media indicates the presence of transformed cells. In a preferred embodiment of using foci formation as the transformation characteristic, test cells are grown with normal cells. As used herein, normal cells are "wild-type" cells, or cells that do not have identifying transformation characteristics as described above. In this manner, the normal cells will form a "lawn" or monolayer of contact inhibited cells. If the test compound is a carcinogen, each test cell will lose contact inhibition and grow to form a focus. If the test compound is non-carcinogenic, the test cells will be contact inhibited just as the normal cells on the lawn and only a monolayer of cells will be seen. This embodiment of the present invention provides several advantages. The normal cells function as "feeder" cells which condition the medium and metabolize the compound being tested. Further, the lawn of normal cells provides a background for comparison of transformed foci. Yet another advantage of the method is that all multi-layered aggregates of cells which overlay the lawn are counted as foci. In this embodiment, the ratio of normal cells to test cells can be between about 100:1 to about 1:1, more preferably from about 50:1 to 5:1, and most preferably about 10:1.

An identifying characteristic of test cell lines of the present invention is that when cultured in the presence of non-genotoxic carcinogens, such as mezerein, teleocidin, okadaic acid, arsenic, vanadate diethylstilbestrol, triethanolamine, clofibrate, di-2-ethylhexyl phthalate, p-dioxane, acetamide, thiourea, dieldrin, 1'-hydroxysafrole, safrole, 1-amino-H-1,2,4-triazole, and 12-O-tetradecanoylphorbol-13-acetate, the cells develop transformation characteristics, such as formation of foci, at a rate which is considered to be statistically significantly higher than the rate at which transformation characteristics are developed in the absence of non-genotoxic and genotoxic carcinogens. More preferably, such cells develop transformation characteristics in the presence of non-genotoxic carcinogens at a rate about 1 fold greater (i.e., 100% increase), more preferably about 25 fold greater, and most preferably about 50 fold greater than in the absence of non-genotoxic and genotoxic carcinogens.

In a further embodiment of the present invention, the occurrence of transformation characteristics is proportional to the carcinogenicity of the compound being tested. That is, the assay method quantifies the carcinogenicity of the compound being tested. In this manner, the relative carcinogenic potential of two different test compounds at a given concentration can be evaluated based on the relative occurrence of transformation characteristics.

As noted above, the present invention involves the use of a recombinant isolated nucleic acid molecule or a modified genome which encodes a protein involved in the transformation of cells. It is to be noted that the term "a" or "an" entity refers to one or more of that entity; for example, an isolated nucleic acid molecule refers to one or more isolated nucleic acid molecules or at least one nucleic acid molecule. As such, the terms "a" (or "an"), "one or more" and "at least one" can be used interchangeably herein. It is also to be noted that the terms "comprising", "including", and "having" can be used interchangeably. The term isolated nucleic acid molecule can include an isolated natural gene which encodes a protein involved in the transformation of a cell, such as a virally derived phosphorylating protein described in more detail below, or a homologue thereof, which is described in more detail below. A nucleic acid molecule of the present invention can include one or more regulatory regions, full-length or partial coding regions, or combinations thereof. The minimal size of a nucleic acid molecule of the present invention is the minimal size that encodes for a protein which is involved in the transformation of cells.

In accordance with the present invention, an isolated nucleic acid molecule is a nucleic acid molecule that has been removed from its natural milieu (i.e., that has been subject to human manipulation). For example, an isolated nucleic acid molecule can be a gene which has been separated from other genes with which it naturally occurs. As such, the term isolated does not reflect the extent to which the nucleic acid molecule has been purified. An isolated nucleic acid molecule can include DNA, RNA, or derivatives of either DNA or RNA.

An isolated nucleic acid molecule of the present invention can be obtained from its natural source either as an entire (i.e., complete) gene or a functional portion thereof. An isolated nucleic acid molecule can also be produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a protein which is involved in transformation of a cell.

A homologue of a nucleic acid molecule which encodes a protein involved in transformation of a cell can be produced using a number of methods known to those skilled in the art (see, for example, Sambrook et al., 1989, *Molecular Cloning: A Laboratory Manual*, Cold Spring Harbor Labs Press.) The reference Sambrook et al., *ibid.*, is incorporated by reference herein in its entirety. For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid.

An isolated nucleic acid molecule of the present invention can include a nucleic acid sequence that encodes at least one protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably. Proteins of the present invention include, but are not limited to, proteins having full-length naturally occurring coding regions, proteins having partial coding regions, fusion proteins, and combinations thereof.

Reference to a nucleic acid molecule which encodes a protein involved in the transformation of a cell refers to nucleic acid molecules that encode proteins which have a function in the mitotic cascade which causes transformation of cells from normal cells to cells having aberrant growth properties as described above or which have a function in initiation or activation of the mitotic cascade (e.g., proteins which control and sense cell-to-cell contact and communication, such as fibronectin receptors, gap junction proteins or transmembrane proteins, can lead to activation of the mitotic cascade). Such nucleic acid molecules can be currently known oncogenes or portions thereof, as well as oncogenes or portions thereof which are identified in the future. Such oncogenes can fall within any recognized class, but generally encode constituents of growth factor signal transduction pathways. While not expressly set forth herein, the present invention includes the use of nucleic acid sequences and molecules of known oncogenes by reference to published literature. For example, they can be genes which encode growth factors (e.g., sis), growth factor receptors (e.g., erbB, fms, trk), intracellular transducers (e.g., src, abl, raf, gsp, ras) or nuclear transcription factors (e.g., jun, fos, myc, erbA). Preferred constituents include intracellular transducers such as phosphorylating proteins, including tyrosine kinases and serine/threonine kinases.

In a preferred embodiment, a nucleic acid molecule of the present invention is virally derived. The nucleic acid molecule can be derived from an RNA or a DNA virus. More particularly, the virally derived transforming protein can be a protein involved with phosphorylation. That is, the mechanism by which the protein transforms cells is by being involved in inappropriate phosphorylation. For example, such protein can be a kinase, which directly phosphorylates another molecule. Alternatively, such a protein can bind to a receptor molecule, such as the PDGF receptor, thereby stimulating autophosphorylation.

Preferred isolated nucleic acid molecules of the present invention can be derived from papilloma viruses, particularly including human, cottontail rabbit and bovine papilloma viruses. More preferably, isolated nucleic acid molecules of the present invention are derived from bovine papilloma virus (BPV). Specifically, the E5, E6 and/or E7 papilloma virus ORFs (open reading frames), and particularly, the BPV E5, E6 and/or E7 ORFs are preferred, with the E5 and particularly, the BPV E5 ORF being most preferred. It should be noted that in addition to these specific ORFs, such preferred isolated nucleic acid molecules of the present invention can also include other portions of viral genomes, including non-coding as well as coding regions or portions thereof.

In a further embodiment, the isolated nucleic acid molecule can be a viral genome or a portion thereof from which portions of the genome have been deleted or inactivated by rearrangement, site-directed mutagenesis or other techniques. More particularly, it has now been recognized that significant advantages can be achieved by tailoring a viral genome for use in a transformation assay by removing portions which are implicated in causing: variation in transformation frequency; spontaneous transformation; instability of viral integration; alteration of nucleic acid copy number; or variation or reduction in sensitivity to carcinogens. For example, virally derived nucleic acid molecules which do not include portions which are responsible for control of copy number, maintenance of the nucleic acid molecule as an episome, and/or integration into the cellular genome, are useful in the present invention. In the instance of nucleic acid molecules derived from papilloma viruses, nucleic acid molecules which do not have functional E1 and/or E2 ORFs (open reading frame) may be useful as nucleic acid molecules of the present invention.

With reference to embodiments of the present invention in which nucleic acid molecules are described by reference to specific known genes, such as the src gene or the BPV E5 gene, such embodiments include not only the specific known molecules, but also nucleic acid molecules which are similar to the referenced genes to a large extent. For example, such nucleic acid molecules include nucleic acid molecules which hybridize with the referenced gene under stringent hybridization conditions. As used herein, stringent hybridization conditions refer to standard hybridization conditions under which nucleic acid molecules, including oligonucleotides, are used to identify molecules having similar nucleic acid sequences. Stringent hybridization conditions typically permit isolation of nucleic acid molecules having at least about 70% nucleic acid sequence identity with the nucleic acid molecule being used as a probe in the hybridization reaction. Such standard conditions are disclosed, for example, in Sambrook et al., *ibid*. Examples of such conditions include, but are not limited to, the following: Oligonucleotide probes of about 18–25 nucleotides in length with $T_m$'s ranging from about 50° C. to about 65° C., for example, can be hybridized to nucleic acid molecules typically immobilized on a filter (e.g., nitrocellulose filter) in a solution containing 5×SSPE, 1% Sarkosyl, 5×Denhardts and 0.1 mg/ml denatured salmon sperm DNA at 37° C. for about 2 to 12 hours. The filters are then washed 3 times in a wash solution containing 5×SSPE, 1% Sarkosyl at 37° C. for 15 minutes each. The filters can be further washed in a wash solution containing 2×SSPE, 1% Sarkosyl at 37° C. for 15 minutes per wash. Randomly primed DNA probes can be hybridized, for example, to nucleic acid molecules typically immobilized on a filter (e.g., nitrocellulose filter) in a solution containing 5×SSPE, 1% Sarkosyl, 0.5% Blotto (dried milk in water), and 0.1 mg/ml denatured salmon sperm DNA at 42° C. for about 2 to 12 hours. The filters are then washed 2 times in a wash solution containing 5×SSPE, 1% Sarkosyl at 42° C. for 15 minutes each, followed by 2 washes in a wash solution containing 2×SSPE, 1% Sarkosyl at 42° C. for 15 minutes each.

The present invention also includes a test cell having a modified genome. As used herein, a modified genome refers to the genome of a test cell in which a portion or portions of the test cell genome is modified in such a way as to make the test cell more susceptible to transformation. The portion or portions of the test cell genome which is modified encodes a protein or proteins which have a function in the mitotic cascade which causes transformation of cells from normal cells to cells having aberrant growth properties as described above or which have a function in initiation or activation of the mitotic cascade (e.g., proteins which control and sense cell-to-cell contact and communication, such as fibronectin receptors, gap junction proteins or transmembrane proteins, can lead to activation of the mitotic cascade). Examples of genes which encode such proteins are given above. Modification of a test cell genome can be accomplished by methods that include, but are not limited to, selective or directed mutation of the above-mentioned portion or portions of the test cell genome or classical genetic selection of naturally occurring mutations.

The present invention also includes a recombinant vector, which includes at least one isolated nucleic acid molecule of the present invention, inserted into any vector capable of delivering the nucleic acid molecule into a test cell. Such a vector contains heterologous nucleic acid sequences, that is nucleic acid sequences that are not naturally found adjacent to nucleic acid molecules of the present invention and that may be derived from a species other than the species from which the nucleic acid molecule(s) are derived. The vector can be either RNA or DNA, either prokaryotic or eukaryotic, and typically is a plasmid or a virus and preferably is a plasmid. One type of recombinant vector, referred to herein as a recombinant molecule and described in more detail below, can be used in the expression of nucleic acid molecules of the present invention.

Suitable and preferred nucleic acid molecules to include in recombinant vectors of the present invention are as generally disclosed herein for suitable and preferred nucleic acid molecules per se. Particularly preferred nucleic acid molecules to include in recombinant vectors, and particularly in recombinant molecules, of the present invention include BPV E5, BPV E6, BPV E7, HPV E5, HPV E6, and HPV E7 from any strain of BPV or HPV, respectively.

A preferred vector of the present invention is identified as plasmid pJS55 which is reported by Sparkowski et al., (1994) "Mutation of the Bovine Papilloma Virus E5 Oncoprotein at Amino Acid 17 Generates Both High- and Low-Transforming Variants", *J. Virol.*, 68:6120–6123, which is incorporated herein by reference in its entirety.

In the present assay, an isolated nucleic acid molecule which encodes a protein involved in the transformation of cells is expressed by culturing a transfected cell capable of expressing the protein under conditions effective to produce the protein. A preferred cell to culture is a recombinant cell that is capable of expressing the protein, the recombinant cell being produced by transfecting a host cell with one or more nucleic acid molecules of the present invention. It should be noted that such a recombinant cell may be repeatedly cloned and selected until such nucleic acid molecule or molecules have stably integrated into the host cell genome. Transfection of a nucleic acid molecule into a cell can be accomplished by any method by which a nucleic acid molecule can be inserted into the cell. Transfection techniques include, but are not limited to, electroporation, $CaCl_2$ precipitation, microinjection, lipofection, adsorption, and protoplast fusion. Suitable and preferred nucleic acid molecules with which to transform a cell are as disclosed herein for suitable and preferred nucleic acid molecules per se. Particularly preferred nucleic acid molecules to include in recombinant cells of the present invention include BPV E5, BPV E6, BPV E7, HPV E5, HPV E6, and HPV E7 from any strain of BPV or HPV, respectively.

Transfected nucleic acid molecules of the present invention can remain extrachromosomal or can integrate into one or more sites within a chromosome of the transfected (i.e., recombinant) cell in such a manner that their ability to be expressed is retained. Preferably, once a host cell of the present invention is transfected with a nucleic acid molecule of the present invention, the nucleic acid molecule is integrated into the host cell genome. A significant advantage of integration is that the nucleic acid molecule is stably maintained in the cell. The nucleic acid molecule can be integrated into the genome of the host cell either by random or targeted integration.

Suitable host cells to transfect include any cell that can be transfected with a nucleic acid molecule of the present invention, including mammalian, avian and herptile, and, preferably, the host cells are mammalian. Host cells can be either untransfected cells or cells that are already transfected with at least one nucleic acid molecule. Host cells of the present invention can be any cell capable of expressing at least one protein of the present invention. Preferred host cells include mouse C127 cells, human newborn foreskin keratinocytes, primary fibroblast cultures of C57BL/6J mice, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, Vero cells, C3H/10T½ cells, and BALB/c3T3 cells. Most preferred host cells include mouse C127 cells, C3H/10T½ cells, human newborn foreskin keratinocytes and primary fibroblast cultures of C57BL/6J mice. Additional appropriate mammalian host cells include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells.

A recombinant cell is preferably produced by transfecting a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transfected into a host cell. As used herein, an expression vector is a DNA or RNA vector that is capable of transfecting a host cell and of effecting expression of a specified nucleic acid molecule. Preferably, the expression vector is also capable of replicating within the host cell. Expression vectors can be either prokaryotic or eukaryotic, and are typically plasmids. Expression vectors of the present invention include any vectors that function (i.e., direct gene expression) in recombinant cells of the present invention, including in mammalian cells.

Recombinant molecules of the present invention may also (a) contain secretory signals (i.e., signal segment nucleic acid sequences) to enable an expressed protein of the present invention to be secreted from the cell that produces the protein and/or (b) contain fusion sequences which lead to the expression of nucleic acid molecules of the present invention as fusion proteins. Recombinant molecules may include intervening and/or untranslated sequences surrounding and/or within the nucleic acid sequences of nucleic acid molecules of the present invention.

Suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments.

Nucleic acid molecules of the present invention can be operatively linked to expression vectors containing regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. In one embodiment, such transcription control sequences can be derived from the same source as the isolated nucleic acid molecule. For example, if the nucleic acid molecule is virally derived or particularly derived from BPV, a suitable transcription control sequence can be virally derived or derived from BPV, respectively. For example, the BPV E2 ORF encodes a protein which stimulates an enhancer and may be a suitable transcription control sequence. Preferred transcription control sequences include those which function in mammalian cells. Such sequences include, but are not limited to, bacteriophage T7 promoter, bacteriophage T3 promoter, metallothionein, promoters of various antibiotic resistance genes, herpesvirus promoters, adenovirus promoters, cytomegalovirus promoters, simian virus 40 promoter, and Rous sarcoma virus promoter.

Transcription control sequences of the present invention can also include naturally occurring transcription control sequences naturally associated with a nucleic acid molecule of the present invention prior to isolation.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transfected, examples of which are disclosed herein.

A recombinant cell of the present invention includes any cell transfected with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transfected with one or more recombinant molecules including nucleic acid molecules encoding one or more proteins of the present invention. In this manner, a transfected cell of the present invention can be transfected with nucleic acid molecules encoding proteins involved in cell transformation through more than one mechanism of cell transformation. For example, a cell of the present invention can be transfected with a nucleic acid molecule which encodes for a phosphorylating protein and for a transcription factor. Such a transfected cell may be either more sensitive to transformation by a potential carcinogen or sensitive to transformation by potential carcinogens which function by different mechanisms or both.

It will be appreciated by one skilled in the art that use of recombinant DNA technologies can improve control of expression of transfected nucleic acid molecules by manipulating, for example, the number of copies of the nucleic acid molecules within a test cell, the efficiency with which those nucleic acid molecules are transcribed, the efficiency with which the resultant transcripts are translated, and the efficiency of post-translational modifications. Recombinant techniques useful for controlling the expression of nucleic acid molecules of the present invention include, but are not limited to, integration of the nucleic acid molecules into one or more test cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the test cell, and deletion of sequences that destabilize transcripts. The activity of an expressed recombinant protein of the present invention may be improved by fragmenting, modifying, or derivatizing nucleic acid molecules encoding such a protein.

In accordance with the present assay, recombinant cells of the present invention are seeded on a culture dish in medium under conditions which promote cell growth and expression of a protein involved in the transformation of cells and in the presence of a compound being tested for carcinogenicity. Effective conditions include, but are not limited to, appropriate media, temperature, pH and oxygen conditions that permit cell growth. An appropriate, or effective, medium refers to any medium in which a cell of the present invention, when cultured, is capable of cell growth and expression of nucleic acid molecules of the present invention. Such a medium is typically a solid or liquid medium comprising growth factors and assimilable carbon, nitrogen and phosphate sources, as well as appropriate salts, minerals, metals and other nutrients, such as vitamins. Culturing is typically conducted in petri plates. Culturing is carried out at a temperature, pH and oxygen content appropriate for the recombinant cell. Such culturing conditions are within the expertise of one of ordinary skill in the art.

The incubation time for growth of cells can vary but is sufficient to allow for the development of transformation characteristics in transformed cells. It will be recognized that shorter incubation times are preferable because compounds can be more rapidly screened for carcinogenicity. In this regard, cell lines of the present invention, under appropriate growth conditions, will develop transformation characteristics in the presence of non-genotoxic carcinogens in less than about 21 days, more preferably less than about 14 days, and even more preferably less than about 10 days.

A further aspect of cell lines of the present invention is that the copy number of the isolated nucleic acid molecule which encodes a protein involved in the transformation of a cell which is transfected into a cell is stable. A significant problem associated with prior known transformation assays is that the viral copy number, in the instance of use of a virally derived protein, can fluctuate wildly. Thus, the ability of such assays to maintain a uniform transformation response after repeated passaging is impaired. In contrast, the present assay involves use of cell lines with stable copy numbers of transfected nucleic acid molecules. In particular, the copy number of transfected nucleic acid molecules in cells of the present invention is typically sufficient to achieve adequate production of the encoded protein. If the nucleic acid molecule is well expressed, the copy number can be as low as one. More preferably, the copy number is typically between about 100 and about 200. Reference to "stable copy number" herein means the copy number remains preferably within at least about 50% of the original copy number over the total number of passages, and more preferably within at least about 25% of the original copy number, and even more preferably, within at least about 10% of the original copy number. The desired copy numbers can be maintained over 5 or more passages of the cell line, and preferably over 10 or more passages, and more preferably over 50 or more passages.

A further aspect of the present invention is a method to identify anti-carcinogenic agents. This method can use materials as described generally herein for other methods of the present invention. The method to identify anti-carcinogenic agents (i.e., transformation inhibitors) can involve the use of test cells which comprise either an isolated nucleic acid molecule which encodes a protein involved in the transformation of a cell or a modified genome which encodes a protein involved in the transformation of a cell, as is described in detail above. In one embodiment, this method includes contacting such a test cell with a known carcinogen. Such a carcinogen can be either a mutagenic or nonmutagenic carcinogen and preferably is a nonmutagenic carcinogen. As used herein, the term "carcinogen" is a compound which causes a cell to demonstrate transformation characteristics in a transformation assay of the present invention. This method further includes contacting such a test cell in the presence of a carcinogen with a compound to be evaluated for its effectiveness as an anti-carcinogenic agent. Such a cell is contacted with both a carcinogen and a compound to be tested in the manner as noted above for other methods of the present invention. After a suitable incubation period, cell growth is scored for the presence or absence of one or more transformation indicators as noted above.

In another embodiment of the method to identify anticarcinogenic compounds, a cell having the phenotype of being transformed in the absence of a known carcinogen is used. Such cells have one or more of the transformation characteristics discussed above. Such cells are known to those skilled in the art, and include, for example, BPV DNA transfected C127 cells. Further, such cells can include cells which are tumorigenic in nude mice. Such a cell is contacted with a compound to be evaluated for its effectiveness as an anti-carcinogenic agent. After a suitable incubation period, cell growth is scored for the presence or absence of one or more transformation indicators as noted above.

The absence of a transformation characteristic or a reduction in the incidence of transformation characteristics compared to the rate of occurrence of transformation characteristics in the absence of the compound being tested, is an indication that the compound being tested is effective as an anti-carcinogenic agent.

Carcinogens which can be used in this embodiment of the present invention can be any known carcinogen, such as mezerein, teleocidin, okadaic acid, arsenic and vanadate. Alternatively, carcinogens can be any other known carcinogen or carcinogens identified in the future.

The foregoing discussion of the invention has been presented for purposes of illustration and description. Further, the description is not intended to limit the invention to the form disclosed herein. Consequently, variation and modification commensurate with the above teachings, within the skill and knowledge of the relevant art, are within the scope of the present invention. The embodiment described hereinabove is further intended to explain the best mode presently known of practicing the invention and to enable other skilled in the art to utilize the invention as such, or other embodiments, and with the various modifications required by their particular application or uses of the invention. It is intended that the appended claims be construed to include alternative embodiments to the extent permitted by the prior art.

What is claimed is:

1. A method to evaluate the carcinogenicity of a compound, said method comprising:
   (a) contacting with said compound being tested for carcinogenicity a test cell transfected with a recombinant nucleic acid molecule from a DNA or RNA virus encoding a transforming protein, wherein said test cell maintains a copy number of said recombinant nucleic acid molecule of within at least about 50% over 5 passages of said test cell;
   (b) scoring cell growth of said test cell based on a transformation characteristic selected from the group consisting of formation of foci, loss of growth factor requirements, loss of serum requirements, tumorigenicity in nude mice and anchorage independence wherein a transformation characteristic of said test cell, compared to a normal cell, indicates that said compound is carcinogenic.

2. The method of claim 1, wherein said transforming protein is selected from the group consisting of proteins which cause transformation of cells from normal cells to transformed cells and proteins which initiate the mitotic cascade which causes transformation of cells from normal cells to transformed cells.

3. The method of claim 1, wherein said transforming protein is selected from the group consisting of growth factors, growth factor receptors, proteins involved in intracellular signal transduction, and nuclear transcription factors.

4. The method of claim 1, wherein said transforming protein is a kinase.

5. The method of claim 1, wherein said recombinant nucleic acid molecule is from a papilloma virus.

6. The method of claim 1, wherein said recombinant nucleic acid molecule is from bovine papilloma virus (BPV).

7. The method of claim 1, wherein said recombinant nucleic acid molecule is from the group consisting of the BPV E5, E6 and E7 open reading frames.

8. The method of claim 1, wherein said recombinant nucleic acid molecule is from the BPV E5 open reading frame.

9. The method of claim 1, wherein said recombinant nucleic acid molecule is a BPV genome in which a viral gene selected from the E1 and E2 open reading frames has been removed or made non-functional.

10. The method of claim 1, wherein said test cell is mammalian.

11. The method of claim 1, wherein said test cell is selected from the group consisting of mouse C127 cells, C3H/10T½ cells, human newborn foreskin keratinocytes and primary fibroblast cultures of C57BL/6J mice.

12. The method of claim 1, wherein said transformation characteristic is formation of foci.

13. The method of claim 12, wherein the step of contacting is conducted in the presence of normal cells.

14. The method of claim 1, wherein said transformation characteristic develops in the presence of a nongenotoxic carcinogen at a rate statistically significantly higher than in the absence of a genotoxic and a nongenotoxic carcinogen.

15. The method of claim 1, wherein said transformation characteristic develops in the presence of a nongenotoxic carcinogen in less than 21 days.

16. The method of claim 1, wherein said test cell maintains a stable copy number of said recombinant nucleic acid molecule.

17. The method of claim 1, wherein said recombinant nucleic acid molecule is from a DNA virus.

18. The method of claim 1, wherein said recombinant nucleic acid molecule is from an RNA virus.

19. A method to evaluate the carcinogenicity of a compound, said method comprising:
   (a) contacting a mammalian test cell transfected with a recombinant nucleic acid molecule encoding a bovine papilloma virus E5 open reading frame with said compound being tested for carcinogenicity;
   (b) scoring cell growth of said test cell for the formation of foci, wherein the presence of foci indicates that said compound is carcinogenic; and
   (c) wherein said test cell maintains a stable copy number of said transfected recombinant nucleic acid molecule over 5 passages of said test cell.

20. A method to evaluate the anticarcinogenicity of a compound, said method comprising:
   (a) contacting with said compound being tested for anticarcinogenicity a test cell transfected with a recombinant nucleic acid molecule of a DNA or RNA virus encoding a transforming protein, wherein said test cell maintains a copy number of said recombinant nucleic acid molecule of within at least about 50% over 5 passages of said test cell; said step of contacting being in the presence of a known carcinogen, wherein in the absence of said compound, said test cell is transformed; and
   (b) scoring cell growth of said test cell based on a transformation characteristic selected from the group consisting of formation of foci, loss of growth factor requirements, loss of serum requirements, tumorigenicity in nude mice and achorage independence, wherein the absence of a compared to a test cell contacted with a known carcinogen in the absence of said compound, indicates that said compound is anticarcinogenic.

21. The method of claim 20, wherein said test cell has the phenotype of being transformed in the absence of a known carcinogen.

22. A method to evaluate the anticarcinogenicity of a compound, said method comprising:

(a) contacting with said compound being tested for anti-carcinogenicity a test cell transfected with a recombinant nucleic acid molecule from a DNA or RNA virus encoding a transforming protein, wherein said test cell maintains a copy number of said recombinant nucleic acid molecule of within at least about 50% over 5 passages of said test cell; wherein said test cell has the phenotype of being transformed in the absence of said compound; and, (b) scoring cell growth of said test cell based on a transformation characteristic selected from the group consisting of formation of foci, loss of growth factor requirements, loss of serum requirements, tumorigenicity in nude mice and anchorage independence, wherein the absence of a transformation characteristic, compared to said test cell in the absence of said compound, indicates that said compound is anticarcinogenic.

* * * * *

UNITED STATES PATENT AND TRADEMARK OFFICE
CERTIFICATE OF CORRECTION

PATENT NO. : 5,821,049
DATED : October 13, 1998
INVENTOR(S) : Kowalski

It is certified that error appears in the above-identified patent and that said Letters Patent is hereby corrected as shown below:

In Claim 20, line 60, between the words "a" and "compared", please insert "transformation characteristic,".

Signed and Sealed this

Twelfth Day of January, 1999

*Attest:*

*Attesting Officer*   Acting Commissioner of Patents and Trademarks